US006958164B2

(12) United States Patent
Dutta-Roy

(10) Patent No.: US 6,958,164 B2
(45) Date of Patent: Oct. 25, 2005

(54) ANTITHROMBOTIC AGENTS

(75) Inventor: Asim Kanti Dutta-Roy, Aberdeen (GB)

(73) Assignee: Provexis Limited, Manchester (GB)

( * ) Notice: Subject to any disclaimer, the term of this patent is extended or adjusted under 35 U.S.C. 154(b) by 262 days.

(21) Appl. No.: 10/442,908

(22) Filed: May 20, 2003

(65) Prior Publication Data

US 2003/0206983 A1 Nov. 6, 2003

Related U.S. Application Data

(63) Continuation of application No. 09/695,739, filed on Oct. 24, 2000, now abandoned, which is a continuation of application No. PCT/GB99/01389, filed on Apr. 23, 1999.

(30) Foreign Application Priority Data

Apr. 24, 1998 (GB) ............................................. 9808796

(51) Int. Cl.$^7$ ............................................. A61K 35/78
(52) U.S. Cl. ................................................... 424/777
(58) Field of Search ........................................ 424/777

(56) References Cited

U.S. PATENT DOCUMENTS

| | | | |
|---|---|---|---|
| 3,864,504 A | 2/1975 | Szabo et al. ................. | 426/373 |
| 4,461,760 A | 7/1984 | Sugano et al. .............. | 424/177 |
| 4,507,286 A | 3/1985 | Vellini .......................... | 514/23 |
| 4,587,124 A | 5/1986 | Kim ........................ | 424/195.1 |
| 5,196,197 A | 3/1993 | Talwar et al. ............. | 424/195.1 |
| 5,284,873 A | 2/1994 | Salinero-Rodero ........... | 514/558 |
| 5,571,675 A | * 11/1996 | Baker et al. ................... | 435/6 |
| 5,571,893 A | * 11/1996 | Baker et al. .................. | 530/350 |
| 5,616,323 A | 4/1997 | Ginoux et al. ............ | 424/195.1 |
| 5,747,043 A | 5/1998 | Ginoux et al. ............ | 424/195.1 |
| 6,555,134 B1 | * 4/2003 | Aviram et al. ............... | 424/456 |

FOREIGN PATENT DOCUMENTS

| | | | |
|---|---|---|---|
| CN | 1226389 | 8/1999 | ............ A23L/1/068 |
| EP | 0 600 544 A1 | 6/1994 | .......... A61K/31/07 |
| FR | 2 143 434 | 2/1973 | ............. A23B/7/00 |
| JP | 59095868 A2 | 6/1984 | ............. A23L/2/26 |
| JP | 59-095869 | 6/1984 | ............. A23L/2/26 |
| JP | 59095870 A2 | 6/1984 | ............. A23L/2/26 |
| JP | 59095871 A2 | 6/1984 | ............. A23L/2/26 |
| JP | 62253368 A2 | 11/1987 | ............. C12G/3/04 |
| JP | 03240469 A2 | 10/1991 | ............. A23L/2/08 |
| JP | 06 046798 A | 2/1994 | |
| WO | WO 95/16363 | 6/1995 | ........... A23L/1/212 |
| WO | WO 97/48287 | 12/1997 | ........... A23L/1/212 |
| WO | WO 99/60868 | 12/1999 | ........... A23L/1/221 |

OTHER PUBLICATIONS

Derwent Abstract XP–002109965: Amor, D., "The case for fruit and vegetables," *J. Fruits, Vegetables and Nuts, Food Industry News*, Nov. 1998.

\* cited by examiner

*Primary Examiner*—Herbert J. Lilling
(74) *Attorney, Agent, or Firm*—Heslin Rothenberg Farley & Mesiti P.C.

(57) ABSTRACT

Methods of prophylaxis or treatment of a disease state initiated by or characterized by platelet aggregation, that employ a fruit extract or active fraction thereof, are disclosed. In one embodiment, the fruit extract or active fraction thereof, is obtained from the fruit of plants of the families Solanaceae, Rutaceae, Cucurbitaceae, Rosaceae, Musaceae, Anacardiaceae, Bromeliaceae, Vitaceae, Arecaceae, Ericaceae and Lauraceae. Pharmaceutical compositions comprising a fruit extract or active fraction thereof having platelet aggregation inhibitory activity are also disclosed.

11 Claims, 8 Drawing Sheets

ANTITHROMBOTIC AGENTS

CROSS REFERENCE TO RELATED APPLICATIONS

This application is a continuation of U.S. patent application Ser. No. 09/695,739 which was filed Oct. 24, 2000 now abandoned as a continuation of International Application PCT/GB99/01389 which was filed Apr. 23, 1999 and claims priority from GB Patent Application GB 9808796.8 filed Apr. 24, 1998. The entire content of the earlier applications is incorporated herein by reference.

FIELD OF THE INVENTION

This invention relates to antithrombotic agents and more particularly to compositions prepared from fruit extracts.

BACKGROUND OF THE INVENTION

It is known that a high consumption of fruits and vegetables is an important preventative measure by which the risk of cardiovascular diseases and certain nutritionally linked cancers, including stomach, colon, breast and prostrate cancer can be reduced. One factor involved in the initiation and development of both cardiovascular diseases and cancers is the occurrence of abnormal oxidative processes leading to the generation of hydroxy and peroxy free radicals or compounds. In part, the beneficial effect of eating fruits and vegetables is explained by the antioxidants contained therein which inhibit oxidative reactions. Specific antioxidants known to account for the inhibition include vitamin C, vitamin E and carotenoids including alpha and beta carotenoids, lycopene, lutein, zeanthin, crytoxanthin and xanthophyllis.

Considerable effort has been expended in identifying nutritional compounds derived from tomato which have a role in the prevention of heart disease and some cancers. Such compounds are disclosed in Abushita et al., *Food Chemistry*, 60:207–12 (1997), wherein a carotenoid extract of tomato was fractionated and the major components identified as lycopene, beta-carotene and lutein.

Studies on tomato have focused on the role of carotenoids, in particular lycopene, in the antioxidant defense against the oxidation of low-density lipoprotein (LDL). Oshima et al.,*J. Agricultural and Food Chemistry*, 44:2306–2309 (1996), disclosed that lycopene supplemental LDL accumulates hydroperoxides more slowly than non-supplemented LDL when challenged by singlet oxygen, thereby providing evidence to support the theory that antioxidants have a hydroxyl/peroxyl radical trapping potential. Furthermore, in Fuhrman et al., Nutrition Metabolism and Cardiovascular Diseases, 1997, 7(6), 433–443, it is disclosed that dietary supplemented lycopene significantly reduced the levels of human LDL oxidation.

In Weisburger, Proceedings for the Society for Experimental Biology and Medicine, 1998, 218(2), 140–143 it is reported that optimal absorption of carotenoids, being typically lipid-soluble chemicals, is improved in the presence of a small amount of dietary oil or fat. Research in the field of nutrition and health has shown that monosaturated oils such as olive oil are most desirable, since such oils do not increase the risk of atherosclerosis, coronary heart disease or nutritionally linked cancers.

SUMMARY OF THE INVENTION

The applicants have found that extracts from many fruits exhibit an ability to inhibit platelet aggregation. The results obtained to date suggest that compositions containing extracts from these fruits may therefore be of use in preventing coronary disease, for example myocardial infarctions and stroke and in preventing further thrombo-embolic events in patients who have suffered myocardial infarction, stroke or unstable angina. In addition, such compositions may be of use in preventing restenosis following angioplasty and bypass procedures. Moreover, compositions comprising fruit extracts may be of use in the treatment of coronary disease resulting from thrombo-embolic disorders such as myocardial infarction in conjunction with thrombolytic therapy.

Results obtained to date indicate that the compounds responsible for the anti-platelet-aggregation activity are water soluble compounds having a very different structure to the lipid soluble compounds such as lycopene identified in the papers referred to above.

There are many known anti-platelet-aggregation agents that act at different stages of platelet production and action. Aspirin (acetylsalicylic acid) is the most widely used and studied. Dipyridamole and ticlopidine have also been used. Aspirin's antiplatelet activity is due to irreversible inhibition of platelet cyclo-oxygenase, thus preventing the synthesis of thromboxane $A_2$, a compound that causes platelet aggregation. Indobufen is a reversible inhibitor of platelet cyclo-oxygenase. Some compounds are direct inhibitors of thromboxane $A_2$ synthase, for example pirmagrel, or act as antagonists at thromboxane receptors, for example sulotroban.

The results obtained to date suggest that the active components in fruit extracts may affect one or more steps of the pathways leading to the production of thromboxane $A_2$ upstream from that of aspirin and the other anti-platelet drugs currently available. It is well known that adverse effects are common occurrences with therapeutic doses of aspirin; the main effect being gastrointestinal disturbances such as nausea, dyspepsia and vomiting. It is anticipated therefore that the isolated platelet aggregation inhibition compounds(s) in fruit extracts will find use as a desirable alternative to aspirin and other antiplatelet drugs in the prevention of thrombo-embolic events and coronary disease.

Accordingly, in a first aspect, the invention provides a fruit extract, active fraction thereof, or one or more active components isolatable therefrom, for use in the prophylaxis or treatment of a disease state initiated or characterised by platelet aggregation.

In another aspect, the invention provides a fruit extract or active fraction thereof or one or more active components isolatable therefrom for use as a platelet aggregation inhibitor.

In a further aspect, the invention provides a fruit extract or active fraction thereof or one or more active components isolatable therefrom for use as an anti-thrombotic agent.

In another aspect, the invention provides the use of a fruit or an extract or active fraction thereof or one or more active components isolatable therefrom as hereinbefore defined for the manufacture of a medicament for use in the prophylaxis or treatment of a disease state initiated or characterised by platelet aggregation; or for use as a platelet aggregation inhibitor; or for use as an anti-thrombotic agent. As used herein the term 'fraction' refers to purified or partially-purified extracts.

In another aspect, the invention provides a process for the manufacture of a medicament for use (i) in the prophylaxis or treatment of a disease state initiated, mediated or characterised by platelet aggregation; or (ii) as a platelet aggregation inhibitor; or (iii) as an anti-thrombotic agent; which process is characterised by the use, as an essential ingredient of the medicament, of a fruit, or an extract or active fraction thereof or one or more active components isolatable therefrom as hereinbefore defined.

In a still further aspect, the invention provides a pharmaceutical composition comprising an active component derived from a fruit or an extract or active fraction or one or more active components isolatable therefrom as hereinbefore defined and a pharmaceutically acceptable carrier.

It is preferred that the fruit extracts used in accordance with the invention are those which are non-toxic to humans, and typically the fruits are those which are usually considered to be edible fruits. Thus the fruits may or may not contain seeds or stones but have an edible essentially non-oily flesh. Typically the fruits can have a rind, shell or skin surrounding the flesh which may optionally be edible.

Examples of fruits that can be used in accordance with the present invention are those selected from the families Solnaceae, Rutaceae, Cucurbitaceae, Rosaceae, Musaceae, Anacardiaceae, Bromeliaceae, Vitaceae, Arecaceae, Ericaceae and Lauraceae.

Examples of Solnaceae include the tomato, for example the English tomato variety. Examples of Rutaceae include the *Citrus* species such as *Citrus paradisi* (grapefruit), *Citrus sinensis* (orange), *Citrus limon* (lemon) and *Citrus aurantifolia* (lime). Examples of Cucurbitaceae include *Cucurnis melo* (melon), e.g. the honeydew melon. Examples of Anacardiaceae include *Mangifera indica* (mango). Examples of Rosaceae include *Pyrus malus* or *Pyrus sylvestris* (apple), *Pyrus communis* (pear), *Amygdalus persica* or *Prunus persica* Var. *nectarine* (nectarine), *Prunus armeniaca* (apricot), *Prunus domestica* (plum), *Prunus avium* (cherry), *Prunus persica* (peach), the strawberry and the blackberry. Examples of Bromeliaceae include *Ananas sativus* (pineapple). Examples of Lauraceae include *Persea gratissima* or *Persea americana* (avocado). Examples of Vitaceae include *Vitis vinifera* (grape). Examples of Arecaceae include *Phoenix dactylifera* (date). Examples of Ericaeae include the blueberry.

Particular examples of fruits, the extracts or active fractions of which have been found to have platelet aggregation inhibitory activity are the tomato, grapefruit, melon, mango, melon, pineapple, nectarine, strawberry, plum, banana, cranberry, grape, pear, apple and avocado.

The extracts of the invention can be prepared by homogenising the flesh of a, preferably peeled, fruit and then removing solids therefrom, for example by means of centrifugation. Thus, the extract is typically an aqueous extract, which can consist essentially of the juice of the fruit, optionally with the addition of extra water added during the homogenising step. Such aqueous extracts can be concentrated, enriched or condensed by, for example, standard techniques, e.g. evaporation under reduced pressure. Examples of concentrates are those which are at least 2-fold concentrated, more usually, at least 4-fold, for example at least 8-fold, or at least 40-fold, or at least 100-fold, or at least 200-fold, or at least 1000-fold.

The extracts can be fractionated to isolate one or more active fractions therein by, for example, molecular weight filtration, or chromatography on a suitable solid support such as a sepharose gel (for size exclusion chromatography) or ion-exchange column using HPLC on a suitably treated silica or alumina, for example ODS coated silica; or by solvent extraction.

Experiments carried out on tomato extracts have revealed that the active component(s) of the extract passes through an ultrafiltration filter having a molecular weight cut-off of 1000, is colourless or straw-coloured, water soluble and does not lose significant activity when boiled.

Accordingly, the invention also provides for use as an antithrombotic agent, or for use as a platelet aggregation inhibitor, or for use in the prophylaxis or treatment of a disease state initiated or characterised by platelet aggregation, an active fraction of a fruit extract, (preferably a tomato extract) the active fraction containing a substantially heat stable colourless or straw-coloured water soluble compound or compounds having a molecular weight of less than 1000.

Tomato extracts, and in particular aqueous extracts of tomato, represent a preferred aspect of the invention. An active fraction of the tomato extract has been found to contain a mixture of nucleosides including cytidine.

Accordingly, one embodiment, there is provided for use as an antithrombotic agent, or for use as a platelet aggregation inhibitor, or for use in the prophylaxis or treatment of a disease state initiated or characterised by platelet aggregation, an active fraction of a tomato extract, the active fraction containing a substantially heat stable colourless or straw-coloured water soluble nucleoside compound or compounds having a molecular weight of less than 1000.

The active fraction has been found to be primarily associated with, or extractable from, the juice, the flesh surrounding the pips, and the pips of tomato. Thus, the use of compositions prepared from an active fraction consisting essentially of a homogenate or an extract thereof derived from the flesh of a peeled tomato or consisting essentially of the juice and/or the flesh surrounding the pips and/or the pips, represents a preferred embodiment of the invention.

The active component of the tomato extract has been analysed by mass spectroscopy (MS) and nuclear magnetic resonance (NMR) spectroscopy and has been found to contain a mixture of nucleosides. In a further aspect, therefore, the invention provides an active fraction per se which is isolatable from tomato and is characterised in that it:

(a) is substantially heat stable
(b) is colourless or straw-coloured;
(c) is a water soluble compound;
(d) consists of components having a molecular weight of less than 1000;
(e) contains one or more nucleosides having platelet aggregation inhibiting activity; and preferably
(f) has a mass spectrum when subjected to MALDI-TOF mass spectrometry, as shown in FIG. 7 appended hereto; and preferably
(g) exhibits a $^1$H nuclear magnetic resonance spectrum substantially as shown in FIG. 6 appended hereto.

Pharmaceutical and Nutriceutical Formulations

The extracts or active fractions thereof can be formulated in a variety of ways. For example, they can be formulated for administration orally, sublingually, parenterally, transdermally, rectally, via inhalation or via buccal administration, but preferably they are formulated for oral or buccal administration. As such, they can be formulated as solutions, suspensions, syrups, tablets, capsules, lozenges, snack bars, inserts and patches by way of example. Such formulations can be prepared in accordance with methods well known per se. It is preferred that the formulations are low in, or substantially free of, lipid materials.

For example, the extracts or active fractions can be formed into syrups or other solutions for administration orally, for example health drinks, in the presence of one or more excipients selected from sugars, vitamins, flavouring agents, colouring agents, preservatives and thickeners.

Tonicity adjusting agents such as sodium chloride, or sugars, can be added to provide a solution of a particular osmotic strength, for example an isotonic solution. One or more pH adjusting agents, such as buffering agents can also be used to adjust the pH to a particular value, and preferably maintain it at that value. Examples of buffering agents include sodium citrate/citric acid buffers and phosphate buffers.

Alternatively, the extracts or active fractions thereof can be dried, e.g. by spray drying or freeze drying, and the dried product formulated in a solid or semi solid dosage form, for example as a tablet, lozenge, capsule, powder, granulate or gel.

Instead simple dried extracts can be prepared without any additional components. Alternatively, dried extracts can be prepared by adsorbing on to a solid support; for example a sugar such as sucrose, lactose, glucose, fructose, mannose or a sugar alcohol such as xylitol, sorbitol or mannitol; or a cellulose derivative. Other particularly useful adsorbents include starch-based adsorbents such as cereal flours for example wheat flour and corn flour. For tablet formation, the dried extract is typically mixed with a diluent such as a sugar, e.g. sucrose and lactose, and sugar alcohols such as xylitol, sorbitol and mannitol; or modified cellulose or cellulose derivative such as powdered cellulose or microcrystalline cellulose or carboxymethyl cellulose. The tablets will also typically contain one or more excipients selected from granulating agents, binders, lubricants and disintegrating agents. Examples of disintegrants include starch and starch derivatives, and other swellable polymers, for example crosslinked polymeric disintegrants such as crosslinked carboxymethylcellulose, crosslinked polyvinylpyrrolidone and starch glycolates. Examples of lubricants include stearates such as magnesium stearate and stearic acid. Examples of binders and granulating agents include polyvinylpyrollidone. Where the diluent is not naturally very sweet, a sweetener can be added, for example ammonium glycyrrhizinate or an artificial sweetener such as aspartame, or sodium saccharinate.

Dried extracts can also be formulated as powders, granules or semisolids for incorporation into capsules. When used in the form of powders, the extracts can be formulated together with any one or more of the excipients defined above in relation to tablets, or can be presented in an undiluted form. For presentation in the form of a semisolid, the dried extracts can be dissolved or suspended in a viscous liquid or semisolid vehicle such as a polyethylene glycol, or a liquid carrier such as a glycol, e.g. propylene glycol, or glycerol or a vegetable or fish oil, for example an oil selected from olive oil, sunflower oil, safflower oil, evening primrose oil, soya oil, cod liver oil, herring oil, etc. Such extracts can be filled into capsules of either the hard gelatine or soft gelatine type or made from hard or soft gelatine equivalents, soft gelatine or gelatine-equivalent capsules being preferred for viscous liquid or semisolid fillings.

Dried extracts can also be provided in a powder form for incorporation in to snack food bars for example fruit bars, nut bars and cereal bars. For presentation in the form of snack food bars, the dried extracts can be admixed with any one or more ingredients selected from dried fruits such as sundried tomatoes, raisins and sultanas, ground nuts or cereals such as oats and wheat.

Dried extracts can be provided in a powder form for reconstitution as a solution. As such they can also contain soluble excipients such as sugars, buffering agents such as citrate and phosphate buffers, and effervescent agents formed from carbonates, e.g bicarbonates such as sodium or ammonium bicarbonate, and a solid acid, for example citric acid or an acid citrate salt.

In one preferred embodiment, dried extract is provided in powder form optionally together with a preferred solid (e.g. powdered) excipient for incorporation into capsules, for example a hard gelatine capsule.

A solid or semisolid dosage form of the present invention can contain up to about 1000 mg of the dried extract, for example up to about 800 mg.

In certain circumstances, it may be desirable to present the extracts for administration by injection or infusion. As such, they will be presented in the form of filtered sterile solutions, preferably in physiological saline buffered to approximately pH 7. Alternatively, they can be presented as sterile powders for making up into injectable or infusible solutions.

The extracts can be presented as food supplements or food additives, or can be incorporated into foods, for example functional foods or nutriceuticals.

The compositions of the invention can be presented in the form of unit dosage forms containing a defined concentration of extract or active fraction thereof. Such unit dosage forms can be selected so as to achieve a desired level of biological activity.

Pharmaceutical Uses

The invention also provides a method for the prophylaxis or treatment of a condition or disorder mediated by platelet aggregation, the method comprising administering to a patient (such as a human or other mammal) in need thereof an effective and preferably non-toxic platelet aggregation inhibiting amount of a fruit or an extract or active fraction thereof as hereinbefore defined.

For the treatment of diseases characterised by platelet aggregation, the quantity of extract or active fraction administered to a patient per day will depend upon the strength of the extract, the particular condition or disease under treatment and its severity, and ultimately it will be at the discretion of the physician. The amount administered however will typically be a non-toxic amount effective to treat the condition in question.

The amount of extract or active fraction administered to a patient typically will vary according to the concentration of the active ingredient or ingredients in the extract. However, a typical daily dosage regime for a human patient suffering from a platelet aggregation mediated disease may be from 0.0001 to 0.1, preferably 0.001 to 0.05 gram per kilogram body weight. When an active fraction is isolated and administered, the amount of solid material administered can be reduced by an amount consistent with the increased purity of the fraction. Typically, administration at least 100 mg, preferably 200 mg of the active fraction per day to a human patient suffering from platelet aggregation mediated disease will inhibit platelet aggregation significantly.

The compositions can be administered in single or multiple dosage units per day, for example from one to four times daily, preferably one or two times daily.

The extracts of the invention can be administered in solid, liquid or semi-solid form. For example, the extracts can be administered in the form of a fruit juice, concentrates of the aqueous extracts or purified active fractions of the extracts in solid, liquid or semi-solid form. When administered in an unconcentrated state they can be administered in the form of a juice prepared from 100% fruit. However, preferably the extracts are administered as concentrates and more preferably as concentrates in solid form for example in the form of tablets, hard gelatine capsules or snack food bars as hereinbefore defined.

In one embodiment of the invention at least 300 ml of 100% fruit juice (for example 600 ml of 100% fruit juice) can comprise a typical daily dosage regime for a human patient suffering from a platelet aggregation associated disease. In another embodiment of the invention, at least 300 ml of 100% fruit juice can be administered in multiple doses per day, for example at least twice a day, preferably three times daily. However, the aforementioned dosage regimens involve the consumption of relative large volumes of liquid which may be unacceptable to the patient. Therefore, in a further embodiment, concentrates as hereinbefore defined can be administered, for example in multiple doses per day.

The extracts of the invention can be administered in conjunction with other therapeutic agents, for example one or more therapeutic agents selected from cardiac or anti-thrombotic agents, antiarrhythmics, ACE inhibitors, beta blockers, vasodilators, other platelet aggregation inhibitors, phosphodiesterase inhibitors, plasminogen activators, and hypolipidaemics by way of example. The extracts can be formulated separately from the other therapeutic agent or they can be formulated together.

The compositions of the invention have platelet aggregation inhibiting activity. As such, the compositions of the invention are useful in the treatment of conditions and disorders in which aggregation of blood platelets play a part, or in which platelet hyperactivity is implicated. Compositions of the present invention may be used therapeutically in various conditions where platelet hyperactivity is a primary or secondary feature such as heart disease, cancers and obesity. Examples of clinical indications in which the compositions of the present invention will be of particular interest include the treatment or management of post myocardial infarction, coronary thromboses, coronary artery by-pass grafts, cardiac valve replacement and peripheral and vascular grafts.

The extracts of the invention can be used alone or in combination with other therapeutic agents. In one preferred embodiment, extracts of the invention are administered in combination with one or more of streptokinase, heparin, insulin, anti-obesity drugs and HMGCoA reductase inhibitors.

BRIEF DESCRIPTION Of THE DRAWINGS

The invention will now be illustrated, but not limited, by the following examples, and with reference to the accompanying Figures of which.

DETAILED DESCRIPTION OF THE PREFERRED EMBODIMENTS

EXAMPLE 1

ADP Induced Platelet Aggregation Study

Methods

Figure 1:
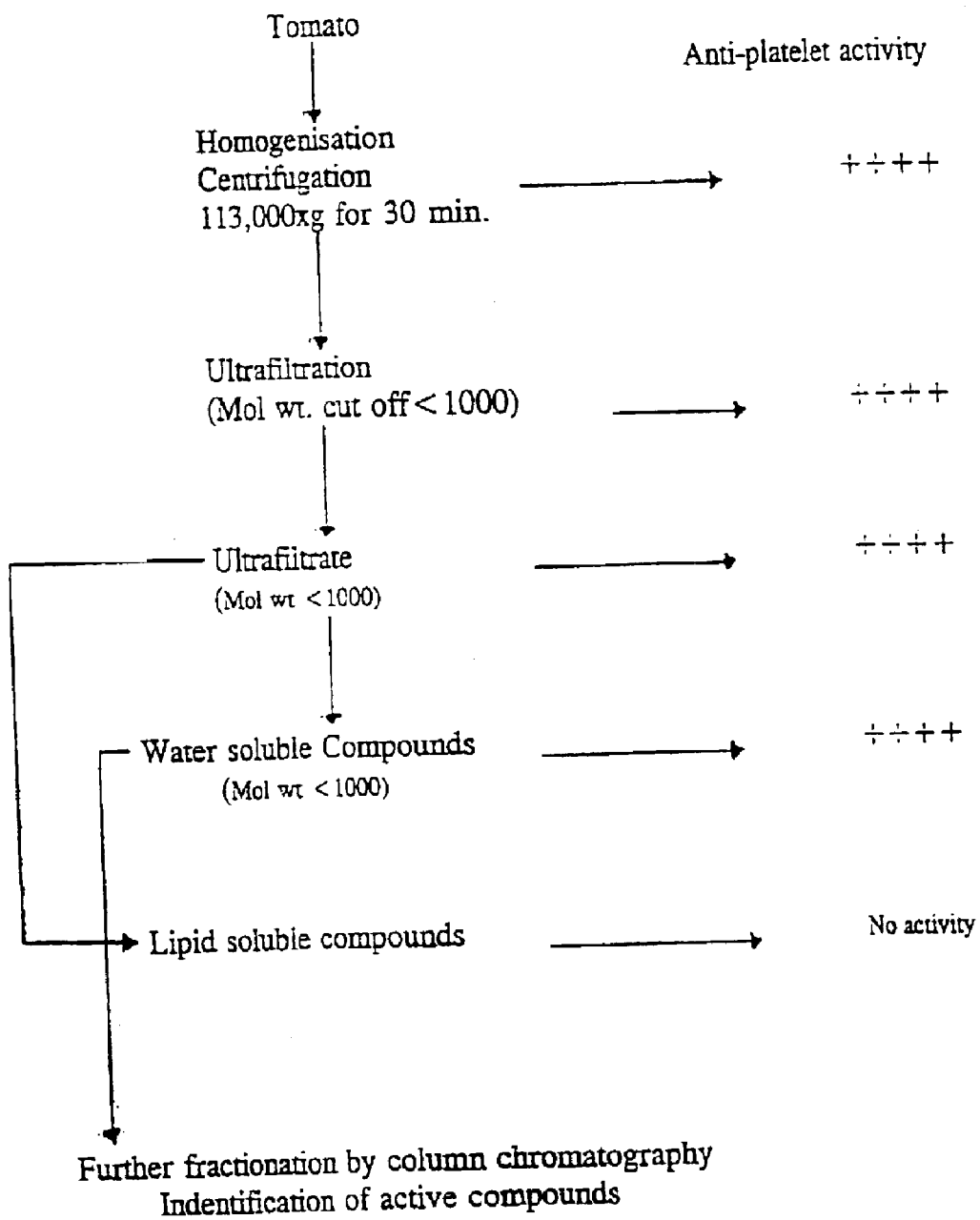
FIG. 1 shows in schematic form a typical procedure for partial fractionation of tomato extracts.

Extracts consisting of 100% fruit juice or diluted fruit juice were freshly prepared on the day of the assay from the fruits set out in Table 1 below. To prepare 100% fruit juice, the fruit were peeled and the flesh was homogenised. The resulting homogenate was spun at 3,000×G for 10 minutes on a centrifuge in 1.5 ml Eppendorf tubes after which the supernatant (juice) was removed and the pH of the juice adjusted to pH 7.4 with either 1M or 0.1M sodium hydroxide depending on the initial pH of the fruit extract. For relatively fibrous fruits (apple, mango, avocado), a 20% or 50% w/v extract was prepared by homogenising either 20% or 50% fruit with phosphate buffered saline (PBS) at pH 7.4, the homogenate being processed as described above in relation to the 100% fruit extracts.

The effect of the fruit extracts on the aggregatory properties of human platelets was investigated in young volunteers. Venous blood was collected from volunteers who had not taken any medication for at least 14 days before donation. Blood (20 ml) was collected using a 19G butterfly needle and coagulation was prevented by mixing the blood samples with Acid Citrate (135 mM) in the ratio of 9 parts by volume of blood to 1 part by volume of ACD). Platelet-rich plasma (PRP) was prepared from the samples by centrifuging the blood at 200 g for 15 minutes.

Fruit juice (50 µl), the pH of which was adjusted to 7.4 where necessary with either 1M or 0.1M sodium hydroxide depending upon the initial pH of the fruit extract, was mixed with the PRP (450 µl) and incubated at 37° C. for 15 minutes, after which the effect of the fruit extract on ADP-induced platelet aggregation was monitored with the addition of ADP to a final concentration of 10 µM. Controls were run in parallel using 50 µl PBS, pH 7.4 instead of the fruit juice.

Platelet aggregation in PRP was monitored using a Packs-4 aggregometer (Helena Labs, USA) at a constant stirring speed of 1000 rpm at 37° C. Platelet counts were performed using a Coulter cell Counter.

Results

Table 1 shows the anti-aggregatory properties of various fruit extracts on human platelets. Results were expressed as % inhibition of aggregation response to ADP, for a number of volunteers (n). In the Table, the extracts marked with an asterisk were boiled for 10 minutes and then centrifuged at 113,000 g for 30 minutes.

TABLE 1

| FAMILY | FRUIT | % FRUIT | % INHIBITION OF AGGREGATION | AVERAGE |
|---|---|---|---|---|
| Solnaceae | tomato (English)* | 100% | 37.7, 82.1, 79.3 | 66.4 |
| Solnaceae | tomato (English) | 100% | 52.3, 63.5, 76.6, 76.3 | 57.9 |
| Rutaceae | grapefruit | 100% | 24.8, 81.8, 34.2, 46.6 | 46.9 |
| Cucurbitaceae | melon (honeydew) | 100% | 43.8, 39.4, 39.0, 47.3 | 42.4 |
| Cucurbitaceae | melon* (honeydew) | 100% | 42.1 | 42.1 |
| Rosaceae | strawberry | 100% | 39.3, 26.6 | 33 |

TABLE 1-continued

| FAMILY | FRUIT | % FRUIT | % INHIBITION OF AGGREGATION | AVERAGE |
|---|---|---|---|---|
| Cucurbitaceae | melon* (Canteloupe) | 100% | 43.2, 14.7 | 29 |
| Cucurbitaceae | melon (Canteloupe) | 100% | 8.9, 43.6 | 26.3 |
| Rosaceae | plum | 100% | 29.8, 22.5 | 26.2 |
| Musaceae | banana | 50% | 18.4, 26.3 | 22.4 |
| Anacardiaceae | mango | 50% | 31.9, 9.2, 25.4 | 22.1 |
| Bromeliaceae | pineapple | 100% | 30.3, 8.8 | 19.5 |
| Rutaceae | orange (Jaffa) | 100% | 17.8, 19.4 | 18.6 |
| — | cranberry | 100% | 18.4 | 18.4 |
| — | cranberry* | 100% | 18.3 | 18.3 |
| Musaceae | banana* | 50% | 16.6 | 16.6 |
| Vitaceae | grape (green) | 100% | 16.4 | 16.4 |
| Rutaceae | grapefruit* | 100% | 15.7 | 15.7 |
| Vitaceae | grape (red) | 100% | 15.0, 12.5 | 13.8 |
| Lanraceae | avocado | 20% | 21.1, 3.3 | 12.2 |
| Rosaceae | nectarine | 50% | 13.2, 6.0 | 9.6 |
| Rosaceae | apple (Granny Smith) | 50% | 5.7 | 5.7 |
| — | cranberry | 50% | 2.6 | 2.6 |
| Rosaceae | pear | 100% | 2.0 | 2.0 |

EXAMPLE 2
Partial Fractionation of Tomato Extract
Methods

Tomato extracts were fractionated according to the general scheme set out in FIG. 1 and the platelet aggregation inhibiting activity measured at various stages. Thus, fresh tomato juice, prepared from 100% fruit, was boiled for 10 minutes and was then centrifuged at 113,000 g for 30 minutes. The platelet aggregation inhibiting activity of the extract is shown in Table 1 above.

Following centrifugation, a portion of the supernatant extract was subjected to ultrafiltration by passing through an Amicon YM1 filtration membrane with a molecular weight cut-off of 1000, under nitrogen pressure at 4° C. The ultrafiltrate was collected, as was any retained fruit juice remaining above the filter (retentate), and the ultrafiltrate and retentate were then both tested for their activities in inhibiting ADP or collagen induced platelet aggregation. The anti-platelet activities of the ultrafiltrate and retentate were the same indicating that the active component of the extract consists of a compound or compounds having a molecular weight of less than 1000.

In order to determine whether the anti-platelet aggregation activity was due to lipid soluble or water soluble components in the tomato ultrafiltrate (molecular weight cut-off 1000), the lipid component of the ultrafiltrate was extracted with chloroform and methanol according the method of Bligh and Dyer. Thus, 2 ml of the ultrafiltrate were mixed with 2.5 ml of methanol followed by 1.25 ml chloroform to give a single phase, and a chloroform:methanol:water ratio of 1:2:0.8. No precipitate was formed. Chloroform (1.25 ml) and water (1.25 ml) were then added to bring the ratio to 2:2:1.8 and, after gentle mixing, the mixture was allowed to settle into two layers. The upper layer (methanol/water) was removed and the methanol blown off under nitrogen at 55° C. The volume was then made up to 2 ml, after adjustment to pH 7.4. The anti-platelet aggregation activity of this aqueous phase was compared with 50 µl of PBS as a control.

The chloroform phase was evaporated under nitrogen, and resuspended in ethanol (50 µl). A sample (10 µl) of the ethanol phase was then tested for anti-platelet aggregation activity versus a 10 µl ethanol control.

Results

The ultrafiltrate (MWCO 1000) and the delipidised aqueous fraction, both at pH 7.4, had similar activity against ADP and collagen induced platelet aggregation. The lipid fraction, on the other hand, did not inhibit primary aggregation, but disaggregation was observed. This was thought to be due to non-specific lipid effects on the platelets.

In conclusion, the fractionation experiments suggested that the platelet aggregation inhibiting activity is associated with water soluble components of a molecular weight of less than 1000. The component(s) is or are heat stable and colourless/straw coloured.

EXAMPLE 3
Isolation and Identification of Active Anti-Platelet Aggregation Component from Tomato Extract
Methods Tomato extracts were fractionated according to the general scheme set out in FIG. 1 and the platelet aggregation inhibiting activity measured at various stages. Thus, fresh tomato juice, prepared from 100% fruit, was boiled for 10 minutes and was then centrifuged at 113,000 g for 30 minutes.

Following centrifugation, a portion of the supernatant extract was subjected to ultrafiltration by passing through an Amicon YM1 filtration membrane with a molecular weight cut-off of 1000, under nitrogen pressure at 4° C. The ultrafiltrate, MWCO 1000, was collected and a sample tested for activity in inhibiting ADP or collagen induced platelet aggregation. The ultrafiltrate was freeze dried for further purification.

The freeze dried sample was suspended in 2 ml water. The anti-platelet aggregation activity of this aqueous phase was compared with 50 µl of PBS as a control. Since only the aqueous fraction of the freeze dried sample has the platelet aggregation inhibiting activity (see Example 2) further purification of the active component was carried out using the aqueous fraction.

Figure 2:
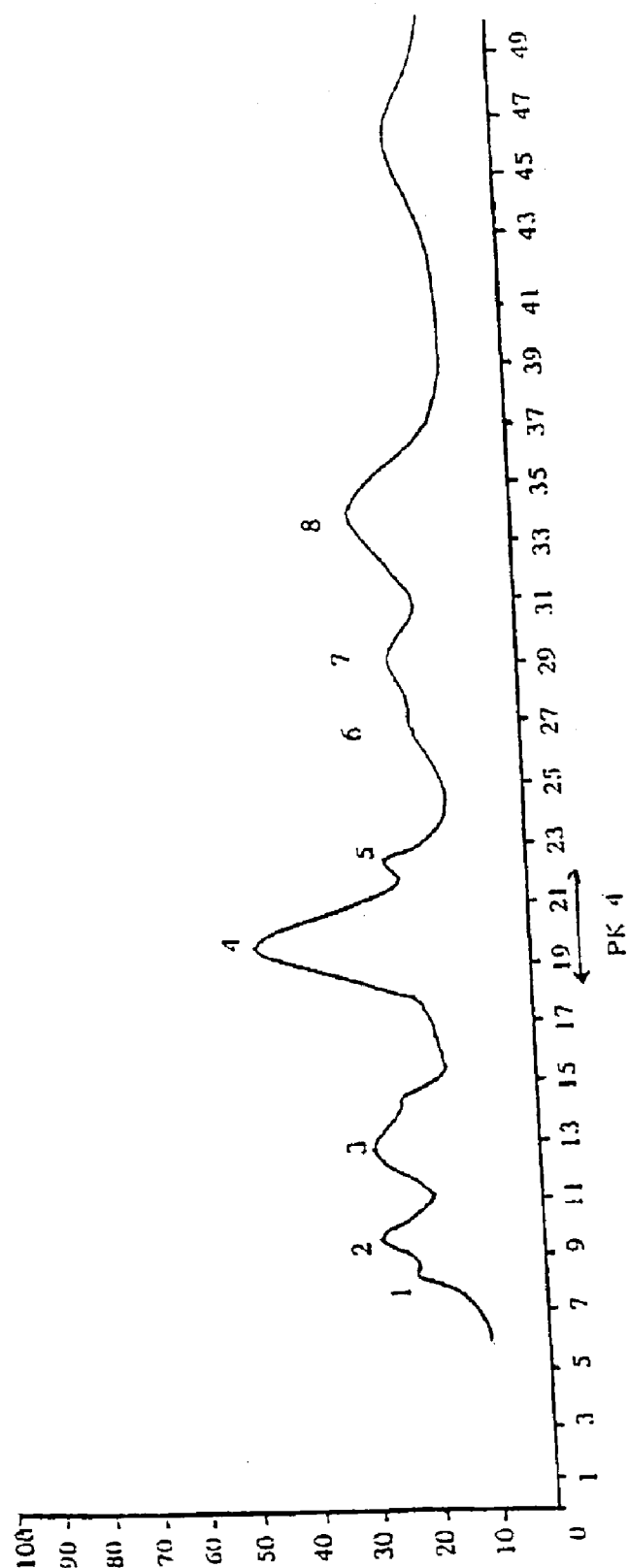
FIG. 2 is a gel filtration chromatogram of an aqueous tomato extract ultrafiltrate.

Further fractionation was carried out on a sepharose column which separates according to molecular size. Thus, gel filtration column chromatography of the resuspended freeze dried sample was carried out using P2 Biogel. A P2 Biogel column was equilibrated with 0.01 M acetic acid buffer, pH 3.3 containing 0.15 M sodium chloride. The sample was loaded on to the column and eluted with a 0.01 M acetic acid buffer, pH 3.3, containing 0.15 M sodium chloride. Platelet aggregation was assayed in each of the fractions collected (designated No 1 to 8) which corresponded to the UV spectra peaks shown on the chromatography trace in FIG. 2.

Platelet aggregation inhibiting activity was found to be concentrated in which one of the fractions collected, which corresponded to Peak 4. This fraction, referred to as Fraction 4, was freeze dried prior to further purification. The freeze dried sample was resuspended in water to give a solution of 20 mg/ml. Desalting of the fraction collected was carried out by loading the sample on to a P2 Biogel column and eluting with 0.01 M acetic acid buffer, pH 3.3. The eluate was freeze dried and resuspended in water as before.

Further purification was achieved by high pressure liquid chromatography (HPLC) ion exchange chromatography on silica gel Nucleosil. The sample was applied onto a Nucleosil 5 µM column with a guard column packed with Persorb A C18. The sample was concentrated on the column by washing the column with solvent A (10 mM sodium acetate adjusted to pH 4 with glacial acetic acid). For elution a linear gradient of 100% solvent A to 100% solvent B (10 mM sodium acetate and 1 M sodium chloride, pH 4) over a time course of 30 min at a flow rate of 1 ml/min.

Two fractions were collected: Fraction 1 which corresponded to material eluted over peaks 1 to 11 (between 2.3 and 8.1 min after sample injection) and Fraction 2 which corresponded to material eluted at peak 5. Desalting of the fractions collected was carried out by loading the sample on to a P2 Biogel column and eluting with 0.01 M acetic acid buffer, pH 3.3. The eluate was freeze dried and resuspended in water as before.

Figure 3:
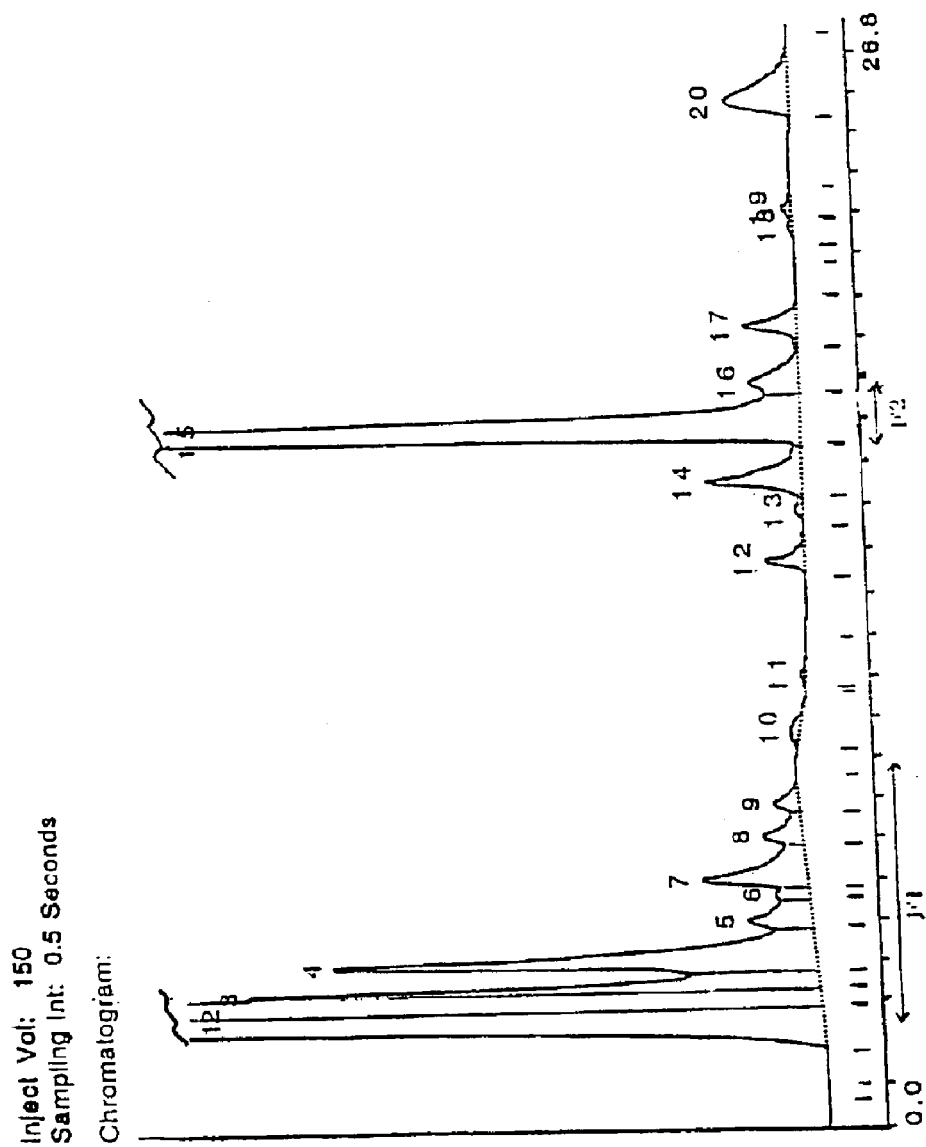
FIG. 3 is a high pressure liquid chromatography (HPLC) ion-exchange chromatogram of a desalted gel-filtered aqueous tomato extract.
Figure 4:
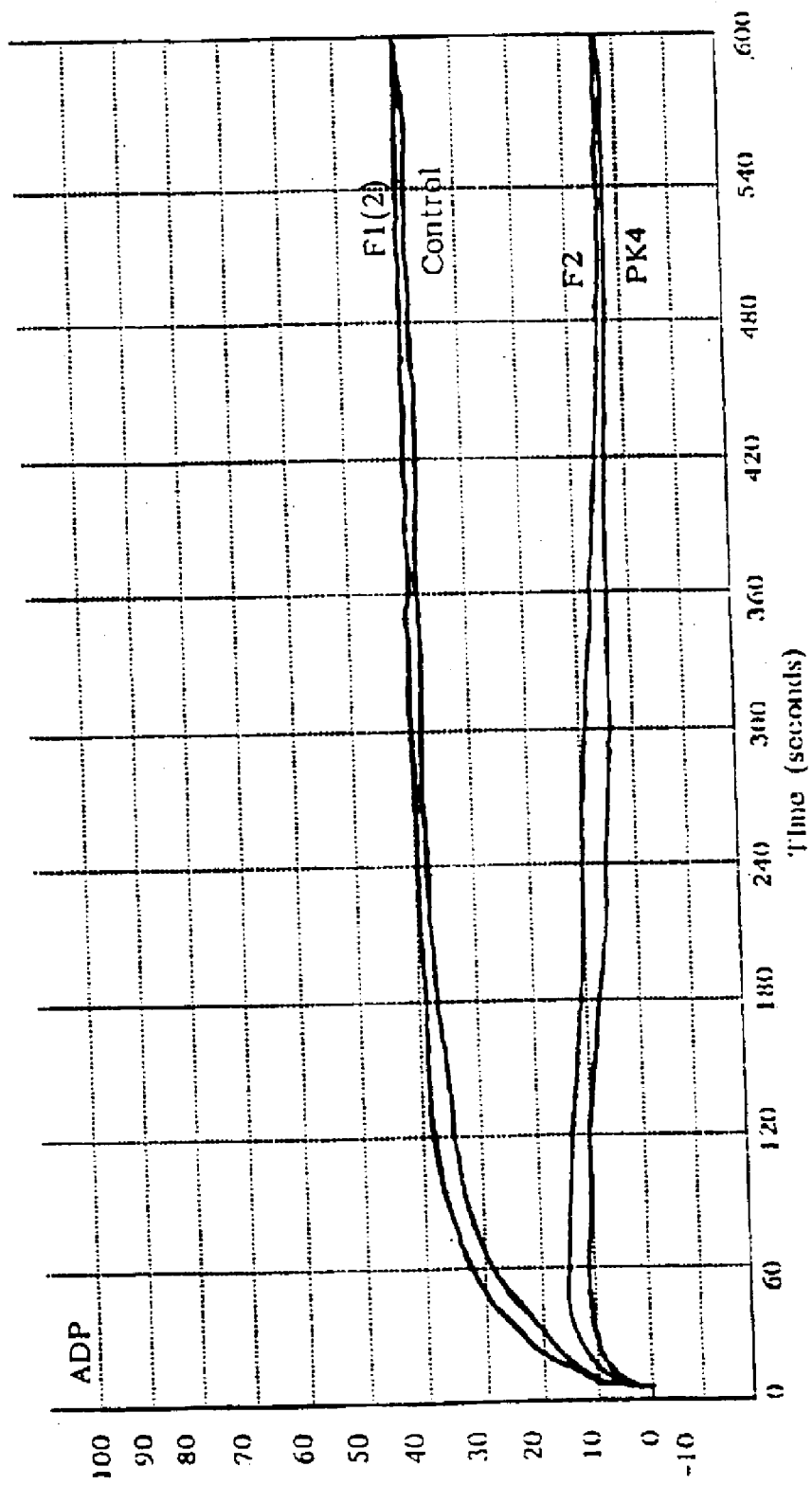
FIG. 4 is a graph showing platelet aggregation activity in desalted fractions, Fraction 1 and Fraction 2, collected following HPLC ion exchange chromatography.

ADP-induced platelet aggregation activity measured in the desalted fractions, Fraction 1 (F1) and Fraction 2 (F2), is shown in FIG. 4. Platelet aggregation inhibiting activity was found to be concentrated in one of the fractions, Fraction 2, which corresponded to peak 15 (FIG. 3). Fraction 2 was then freeze dried prior to further analysis. The freeze dried sample was resuspended in water to give a concentration of 20 mg/ml and retained for structural analysis of the active component(s).

The active components present in the active fraction were characterised using mass spectroscopic and nuclear magnetic resonance (NMR), as described below.

Nuclear Magnetic Resonance Spectroscopy

Figures 5, 6:
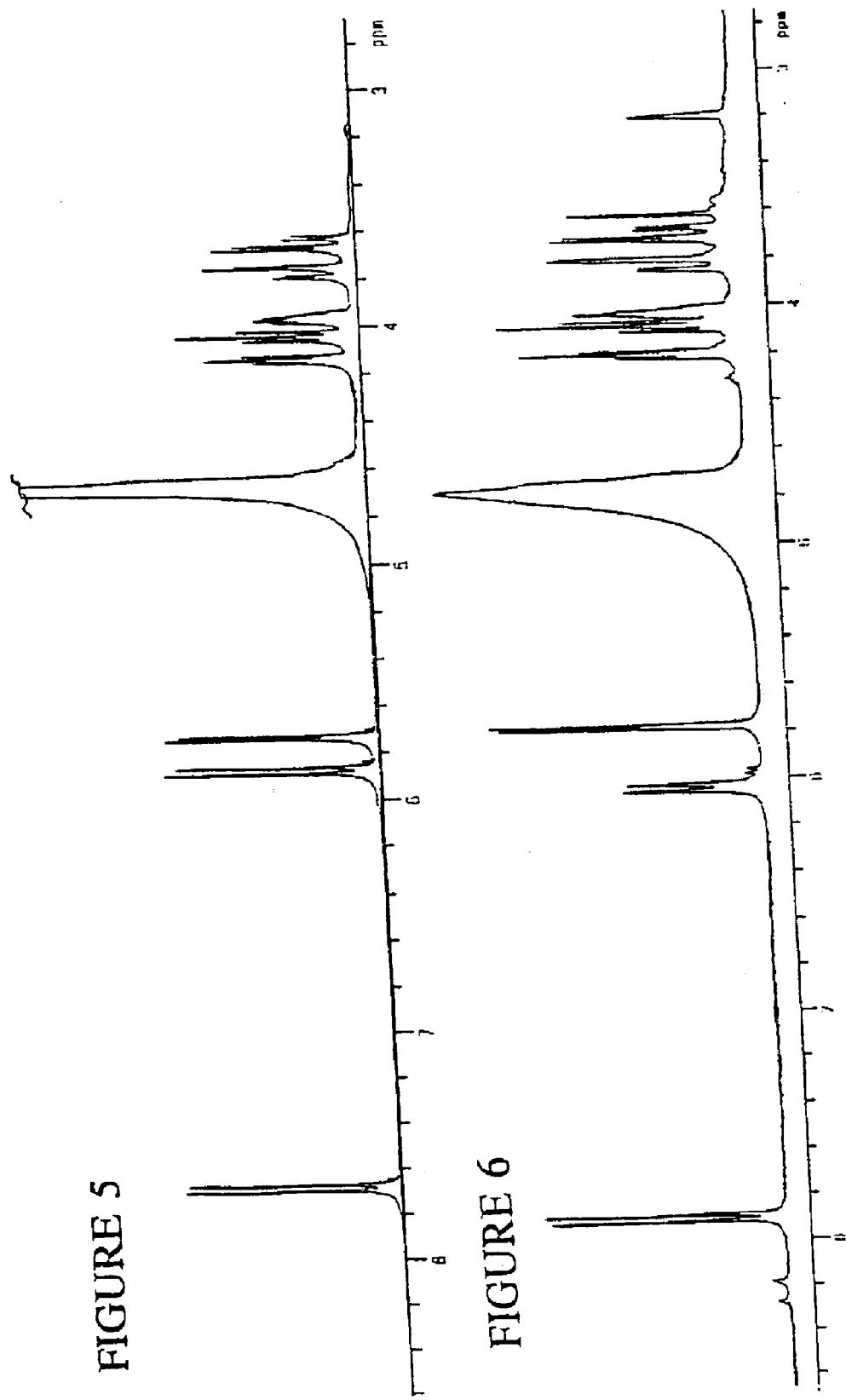
FIG. 5 is a $^1$H NMR spectrum of cytidine.
FIG. 6 is a $^1$H NMR spectrum of a desalted active Fraction F2 of an aqueous tomato extract.

A portion of the sample of active fraction F2 was subjected to $^1$H NMR analysis and the resulting NMR spectrum is shown as FIG. 6. The spectrum of the active fraction was compared with the spectrum of a pure sample of the compound 4-amino-1-B-D-ribofuranosyl-2-(1H)-pyrimidinone (cytidine)—see FIG. 5, from which it can be seen that there are considerable similarities but clearly the active fraction does not contain pure cytidine. The NMR data for sample F2 suggested the presence of ribose. The minor differences in the NMR data suggested a different pH or a different salt.

Mass Spectroscopic Analysis

The desalted active fraction, fraction 2 (F2), was subjected to a number of mass spectroscopic analytical techniques. The data obtained from the various mass spectra suggested that sample F2 contains several nucleoside species, of which the major component is cytidine.

Probe EIMS

A portion of sample F2 (42480) was examined by probe EIMS using a temperature ramp of ambient ca. 550° C. at 50° C. per minute. VG AutoSpecE mass spectrometer was used, scanning from 950 to 25 amu at ca. five seconds per scan. The probe EIMS data for F2 showed a potentially diagnostic ion at m/z 111 which appeared to correspond to 4-aminopyrimidinone (cytosine) formed by thermal/EI-induced fragmentation of a nucleoside, by comparison with a NIST library EI mass spectrum of cytosine. There was also clear evidence for the presence of HCl, suggesting a hydrochloride. The sample appeared to be contaminated with branched oligomers of octylphenol ethoxylates, giving ions at m/z 45, 135, 267, 311, 355, 382, 399, 426, 443, 470 and 487.

MALDI-TOF

Portions of sample F2 (42480) and various standards including cytidine were dissolved in water and mixed with matrix (9:1 5-hydroxypicolinic acid/50 mM ammonium citrate). A PE Biosystems Voyager-STR mass spectrometer was used. A matrix blank was also analysed. The MALDI-TOF (matrix assisted laser desorption/ionisation-time of flight) spectrum of sample F2 (FIG. 7) was closely similar to that of cytidine and arabinofuranosyl cytosine. All three samples showed clear m/z 244 (MH$^+$), m/z 266 (MNa$^+$), m/z 487 (2MH$^+$) and m/z 509 (2MNa$^+$) ions suggesting that the main component of F2 is cytidine or an isomer of cytidine. Cyclocytidine had a lower molecular weight, as expected and showed ions at m/z 266 (MH$^+$), m/z 451 (2MH$^+$) and m/z 473 (2MNa$^+$).

Derivatisation/GC-EIMS

Portions of sample F2 (42480) and various standards including cytidine were dissolved in water and mixed with internal standard (arabitol). The resulting solutions and a blank were lyophilised, N-acetylated using acetic anhydride/pyridine and trimethylsilylated using Tri-Sil-Z. The resulting products were dissolved in hexane and aliquots (ca. 1 μl) analysed by GC-EIMS (gas chromatography—electron ionisation mass spectroscopy) on a VG Trio-1 benchtop mass spectrometer. The samples were injected via a cold on-column injector onto a DB-5 capillary GC column. The GC-EIMS data from derivatised sample F2 and a derivatised cytidine control sample suggested that the main component in sample F2 is closely similar to derivatised cytidine, but subtly different to derivatised arabinofuranosyl cytosine.

Derivatisation/GC-CIMS

Portions of sample F2 (42480) and the cytidine standard were dissolved in water and lyophilised. They were derivatised in the same manner as above and aliquots (ca. 1 μl) of the resulting hexane solutions analysed by GC-CIMS (gas chromatography—chemical ionisation mass spectroscopy) on a PE TurboMass benchtop mass spectrometer. The samples were injected via a PSS injector onto a DB-5MS capillary GC column. The GC-CIMS data for derivatised F2 and derivatised cytidine confirmed that one of the peaks in sample F2 is cytidine. Examination of the CI spectra also revealed the presence of ions at m/z 259 and 348, which can be associated with the ribofuranosyl unit.

EXAMPLE 4

Assay of the Activity of Tomato-Derived Extract in Inhibiting Platelet Aggregation Induced by Agonists or After the Addition of Arachidonic Acid It is known that following injury, platelets adhere to the damaged vascular endothelium thereby facilitating further platelets to stick to one another, aggregate, become activated and form a platelet plug. Platelet aggregation is mediated via factors which are produced at the site of injury and react with receptors on the platelet surface. Some of these factors for example ADP, serotonin and thromboxane $A_2$ are themselves released by activated platelets, producing a positive feedback loop.

During the process of platelet aggregation and activation, ligands such as ADP, or collagen in low doses, bind to specific receptors. This leads to activation of membrane phospholipases and the release of arachidonic acid from the platelet membrane phospholipids by the activity of the enzyme phospholipase A2. A proportion of arachidonic acid is then rapidly metabolised by several cyclic endoperoxidases, the major ones being cylco-oxygenase and lipoxygenase, to prostaglandins and finally to thromboxane $A_2$ via the enzyme thromboxane synthetase. Thromboxane $A_2$ is biologically highly active and mediates a rise in intracellular calcium ions and platelet granule release which promotes further platelet aggregation. Thromboxane $A_2$ is chemically unstable and breaks down to thromboxane $B_2$ and therefore measurement of thromboxane levels is carried out by measuring thromboxane $B_2$.

The platelet aggregation inhibiting activity of semi-purified tomato extracts was assayed by measuring the production of thromboxane $B_2$ produced by platelets in the presence of agonists ADP or collagen or when exogenous arachidonic acid is added.

Methods

Semi-purified tomato extracts were prepared according to Examples 2 and 3. Thus, 50 μl of the gel filtration fraction corresponding to Peak 4 (see FIG. 2) or HPLC-purified Fraction 2 (see FIG. 3) were added to 50 μl PBS buffer and incubated with 450 μl platelet-rich plasma for 15 min at 37° C. Following incubation, the agonist was added to the desired concentration. The assay mixture was then centrifuged and the levels of thromboxane $B_2$ in the supernatant measured. Alternatively, the centrifuged assay samples were rapidly frozen for thromboxane $B_2$ analysis at a later date.

Results

TABLE 2

| Sample | Agonist | Thromboxane $B_2$ |
|---|---|---|
| Control | ADP (10 μM) | 12.31 ng/ml |
| Peak 4 | ADP | 3.11 |
| Control | ADP | 24.43 |
| Peak 4 | ADP | 5.06 |
| F2 | ADP | 4.60 |
| Control | ADP | 10.62 |
| F2 | ADP | 3.51 |
| Control | Collagen (2 μg/ml) | 116.72 |
| F2 | Collagen | 50.50 |
| Control | ADP | 10.26 |
| F2 | ADP | 3.11 |
| F2 | ADP | 4.82 |
| Control | Arachidonic acid 0.5 mg/ml | 315.46 |
| F2 | Arachidonic acid | 315.46 |
| Control | Collagen | 113.79 |
| F2 | Collagen | 61.56 |

Table 2 shows the effect of the gel filtration fraction corresponding to Peak 4 and the HPLC Fraction F2 fraction, on thromboxane $B_2$ production in platelets by ADP, collagen and arachidonic acid. Results were expressed as nanogramme/ml thromboxane $B_2$ produced in response to ADP, collagen or arachidonic acid in the presence of the semi-purified tomato extract.

The gel filtration fraction corresponding to Peak 4, Fraction 4, and the HPLC Fraction, Fraction 2, had similar potency against ADP induced thromboxane $B_2$ production. Similarly, the Fraction 2 inhibited collagen induced thromboxane $B_2$ production when compared to the control sample. Fraction 2, on the other hand, did not inhibit thromboxane $B_2$ production in the presence of arachidonic acid.

Conclusion

These experiments showed that the active component(s) of tomato juice extract inhibits production of thromboxane $B_2$ induced by ADP and collagen, but does not stop metabolism of arachidonic acid to thromboxane $B_2$. The results suggest that the platelet aggregation inhibiting activity does not block the conversion of arachidonic acid to thromboxane $A_2$ and as such does not inhibit the activity of the enzyme cyclo-oxygenase catalysing this conversion.

In conclusion, the results of this experiment suggest that the activity of the active anti-platelet aggregation component in tomato extracts is different from that of aspirin.

EXAMPLE 5

Location of the Active Component in Tomatoes

Four tomatoes were peeled and dissected to obtain preparations containing the following:

i) the juice surrounding the seeds; referred to as T1
ii) tomato flesh only; referred to as T2
iii) whole tomatoes including the seeds; referred to as T3.

Extracts of preparations T1 to T3 were prepared as described in Example 1 and ADP induced platelet aggregation activity was measured in each.

Results and Conclusions

Figure 9:
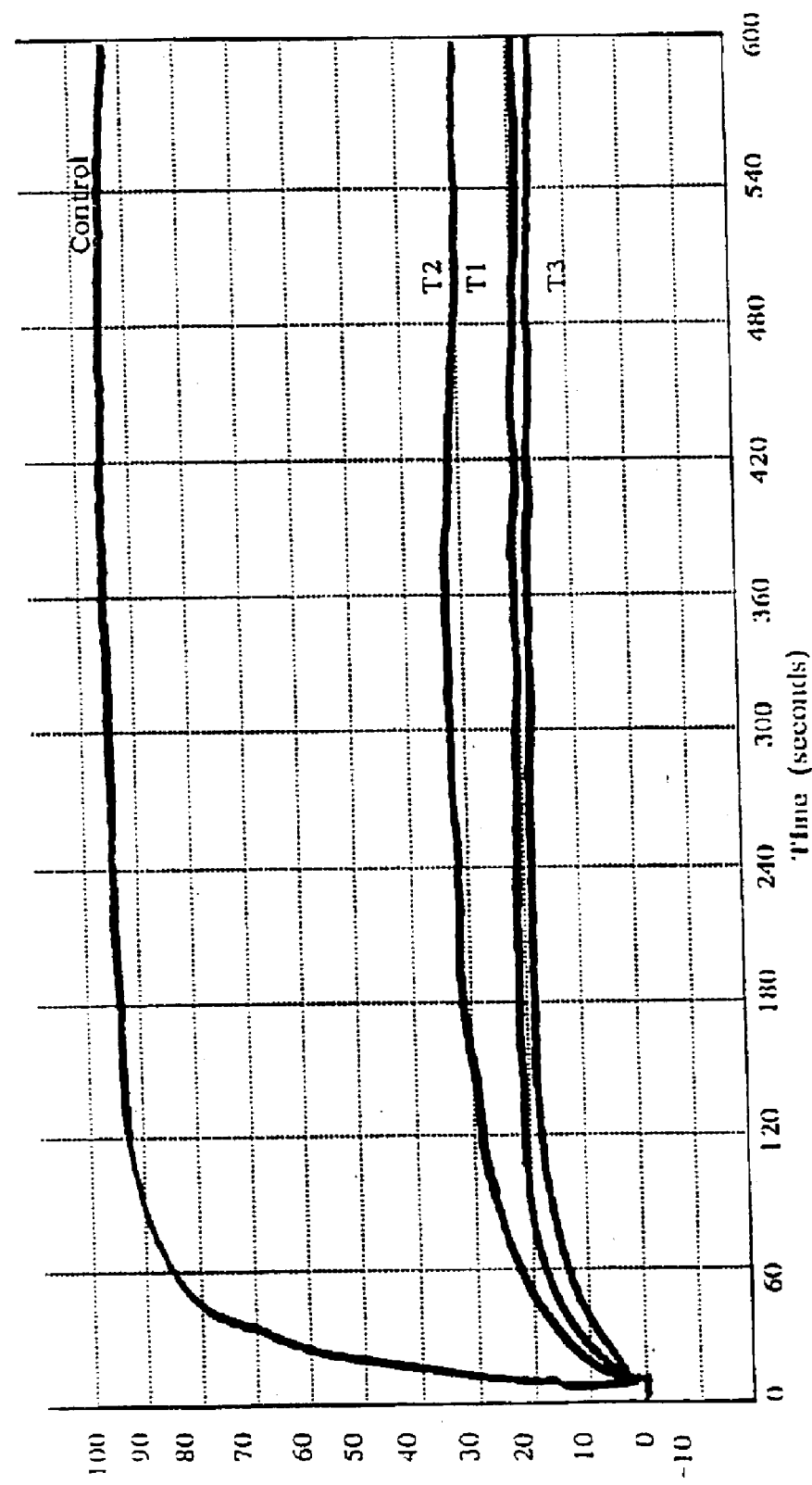
FIG. 9 is a graph showing the platelet aggregation assay results obtained using extracts from different parts of the tomato.

FIG. 9 shows the anti-platelet aggregation activity of the tomato preparations T1 to T3 on human platelets. Preparations T1 and T3 had similar potency against ADP induced platelet aggregation. Moreover the platelet aggregation activity measured in T1 and T3 was much reduced compared to T2 suggesting that the active anti-platelet aggregation component is localised to a greater degree in the juice and the seeds of the tomato.

EXAMPLE 6

Bioavailability Studies

Preliminary studies on the bio-availability of the active platelet aggregation inhibiting component in tomato extracts were performed on four volunteers. Dosages of 300 ml of 100% tomato juice prepared as described in Examples 1 and 2 were fed to each of four volunteers. Platelet aggregation activity was measured in venous blood samples taken from volunteers immediately before (time 0), and one hour following (time 1), consumption of the juice.

Table 3 shows the percentage reduction in ADP-induced and collagen-induced platelet aggregation activity in blood samples taken from each of four individuals one hour after consumption of the tomato juice preparation. The results suggest that the consumption of 300 ml of tomato juice is sufficient to significantly reduce platelet aggregation.

TABLE 3

| | Volunteer | | | |
| Agents | 1 | 2 | 3 | 4 |
|---|---|---|---|---|
| Collagen (2 μg ml$^{-1}$) | 95% | 27.6% | 6.8% | 4.3% |
| ADP (7.5 μM) | 12.9% | 21.6% | 8.1% | 8.4% |

EXAMPLE 7

Investigation of Cumulative Effect of Consumption of Tomato Juice 300 ml of tomato juice prepared in accordance with Example 6 was fed daily to two individuals over a two-week period. Measurements of platelet aggregation activity revealed that there was approximately 12% inhibition of platelet aggregation as compared to Day 0 and the activity was not retained, i.e. not accumulated in the body.

Formulations

EXAMPLE 8

Capsules Containing Fruit Extract

A capsule formulation is prepared by freeze drying a fruit extract (e.g. a tomato extract as described in Examples 2 and/or 3) and filling the resulting freeze dried powder into a hard gelatin capsule shell to give a capsule content of 800 mg per capsule.

EXAMPLE 9

Capsules Containing Diluted Fruit Extract

To an aqueous solution of the active fraction of Example 2 or Example 3 is added a diluent selected from sucrose, lactose and sorbitol. The solution is then freeze dried to give a powder which is filled into hard gelatin capsule shells to give a capsule content of 800 mg per capsule (200 mg tomato extract and 600 mg diluent).

EXAMPLE 9

Chewy Fruit Bar Containing Dried Fruit Extract

A chewy food bar is prepared by combining freeze dried tomato extract powder with oat flour and mixing together with the other ingredients in a mixer, compressing into a bar shape and baking.

|  | Grams per bar |
|---|---|
| Active Constituent | |
| Dried tomato extract | 10 |
| Other Constituents | |
| Raisins | 30 |
| Rolled oats | 20 |
| Oat flour | 20 |
| Honey | 10 |
| Hazel nuts | 10 |
| Vegetable oil | 10 |
| Glucose syrup | 10 |
| Sugar | 10 |
| Malt extract | 5 |
| Cornflour | 5 |
| Whey powder | 1 |
| Salt | 1 |

The invention has been illustrated by reference to particular examples but it will readily be appreciated that numerous modifications and alterations may be made without departing from the scope of the claims appended hereto.

I claim:

1. A method for the prophylaxis treatment of a condition or disorder mediated by platelet aggregation, the method comprising administering to a patient in need of such treatment, a therapeutically effective amount of a fruit extract having platelet aggregation inhibiting activity, the fruit extract being a water soluble extract of tomato; wherein the extract contains an active fraction having active components that are capable of passing through an ultrafiltration filter having a molecular weight cut-off of 1000, the active fraction containing one or more nucleosides having platelet aggregation inhibiting activity; and wherein the extract has been prepared by a process comprising the steps of homogenizing the flesh of a tomato to form a homogenate and removing solids therefrom to give an aqueous extract.

2. A method according to claim 1, wherein the tomato is peeled prior to the step of homogenizing.

3. A method according to claim 1, wherein the extract is in the form of a concentrate or a dehydrate.

4. A method according to claim 3, wherein the extract is in the form of a concentrate which is at least 2-fold concentrated.

5. A method according to claim 3, wherein the extract has been dehydrated to give a dry extract.

6. A method according to claim 5, wherein the dry extract is in the form of a solid or semisolid dosage form.

7. A method according to claim 6, wherein the extract is contained within a capsule shell.

8. A method according to claim 1, wherein the active fraction of the extract is substantially heat stable and is colorless or straw-colored.

9. A method according to claim 1, wherein the condition or disorder is selected from the group consisting of myocardial infarction, stroke, cardiovascular disease, and disease states associated with platelet hyperactivity.

10. A method according to claim 1, wherein the active fraction exhibits an $^1H\_NMR$ spectrum substantially as shown in FIG. 6.

Figure 7:
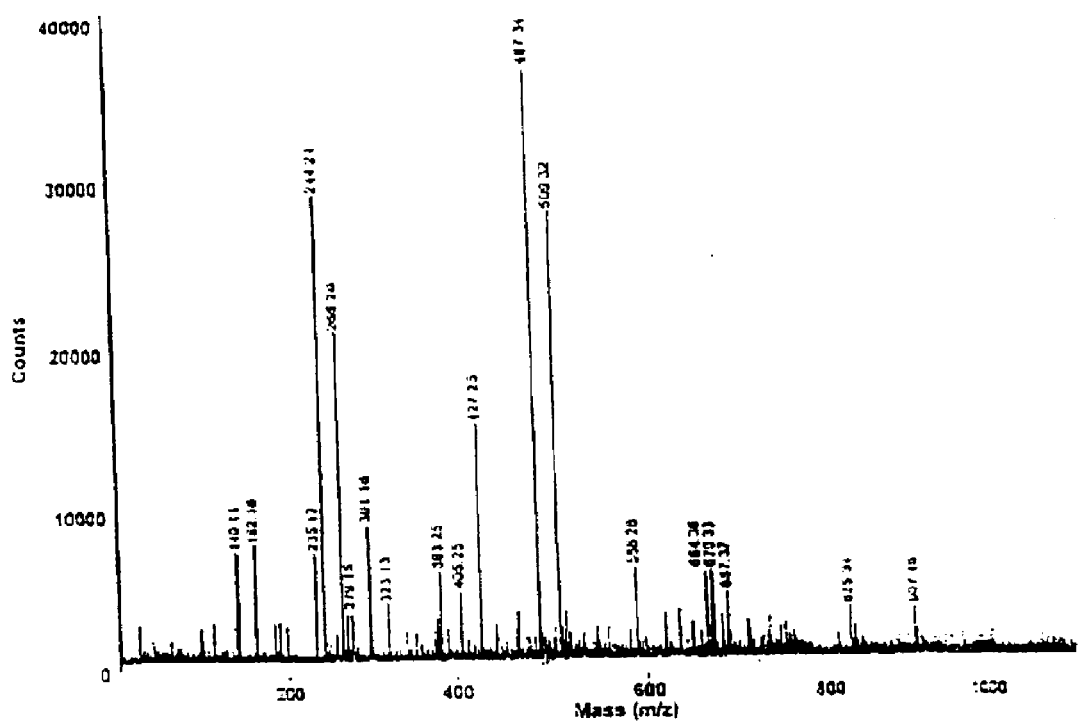
FIG. 7 is a MALDI-TOF mass spectrum of the active fraction F2.
Figure 8:
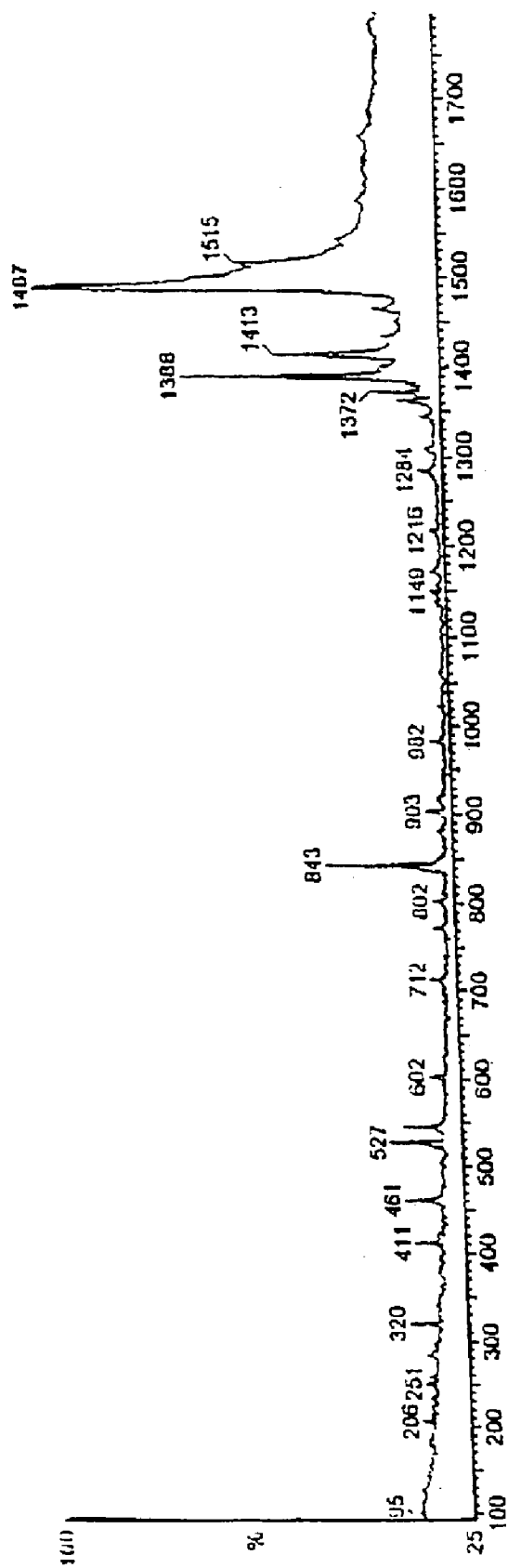
FIG. 8 is a GC-CIMS chromatogram of derivatised fraction F2.

11. A method according to claim 1, wherein the active fraction has a mass spectrum as shown in FIG. 7, when subjected to MALDI-TOF mass spectrometry.

* * * * *

UNITED STATES PATENT AND TRADEMARK OFFICE
CERTIFICATE OF CORRECTION

PATENT NO. : 6,958,164 B2
DATED : October 25, 2005
INVENTOR(S) : Dutta-Roy

It is certified that error appears in the above-identified patent and that said Letters Patent is hereby corrected as shown below:

Column 16,
Line 28, delete "$^1$H_NMR" and insert -- $^1$H NMR --.

Signed and Sealed this

Twenty-seventh Day of December, 2005

JON W. DUDAS
*Director of the United States Patent and Trademark Office*